__United States Patent__ [19]

Gibbs et al.

[11] Patent Number: 4,665,098

[45] Date of Patent: May 12, 1987

[54] PHARMACEUTICAL COMPOSITION OF N-(4-HYDROXYPHENYL) RETINAMIDE HAVING INCREASED BIOAVAILABILITY

[75] Inventors: Irwin S. Gibbs, Huntington Valley; Pramod M. Kotwal, Blue Bell, both of Pa.

[73] Assignee: McNeilab, Inc., Fort Washington, Pa.

[21] Appl. No.: 717,252

[22] Filed: Mar. 28, 1985

[51] Int. Cl.⁴ ............................................. A61K 31/16
[52] U.S. Cl. ................................................... 514/613
[58] Field of Search ......................................... 514/613

[56] References Cited

U.S. PATENT DOCUMENTS 4,190,594  2/1980  Gander et al. .................... 260/404
4,323,581  4/1982  Gander ............................. 424/324

OTHER PUBLICATIONS

"Pharmacokinetics of N-(4-Hydroxyphenyl)-all-trans-Retinamide in Rats", Brian N. Swanson et al., Laboratory of Chemoprevention, National Cancer Institute, vol. 8, No. 3, (1979), pp. 168-172.

"N-(4-Hydroxyphenyl)retinamide, A New Retinoid for Prevention of Breast Cancer in Rat", Richard C. Moon et al., IIT Research Institute, Chicago, IL, vol. 39, (1979), pp. 1339-1346.

"Biopharmaceutics of Drugs Administered in Lipid--Containing Dosage Forms I; GI Absorption of Griseofulvin from an Oil-in-Water Emulsion in the Rat", Philip J. Carrigan et al., Journal of Pharmaceutical Sciences, vol. 62, No. 9, (1973), pp. 1476-1479.

"The Theory and Practice of Industrial Pharmacy", Leon Lachman et al., Lea & Febiger, Philadelphia, (1970), pp. 359-384.

"Effect of Lipid Vehicles on the Oral Absorption of a Model Compound (DDT)", K. Palin et al., J. Pharm. Pharmacol., (1980), vol. 32, Supplement p. 62P.

"Hypotensive Action of Commercial Intravenous Amiodarone and Polysorbate 80 in Dogs", William B. Gough et al., Journal of Cardiovascular Pharmacology, vol. 4, p. 375, (1982).

"Communications, 'Effect of Formulation on the Bioavailability of Retinol, D-α-Tocopherol and Riboflavine' ", N. E. Bateman et al., J. Pharm. Pharmacol., (1984), vol. 36, pp. 461-464.

Primary Examiner—Jerome D. Goldberg
Attorney, Agent, or Firm—David J. Levy

[57] ABSTRACT

A dosage of N-(4-hydroxyphenyl)retinamide, also known as fenretimide, of the following formula:

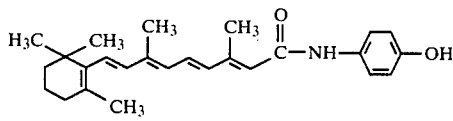

with increased bioavailability comprising corn oil and a non-ionic surfactant. The formulation if useful in the treatment of breast or bladder cancer, psoriasis and acne.

13 Claims, No Drawings

PHARMACEUTICAL COMPOSITION OF N-(4-HYDROXYPHENYL) RETINAMIDE HAVING INCREASED BIOAVAILABILITY

BACKGROUND OF THE INVENTION

N-(4-Hydroxyphenyl)-all-trans-retinamide, also known as HPR or fenretinide and having CAS registry number 65646-68-6, is described in U.S. Pat. Nos. 4,190,594 and 4,323,581 and has the following formula:

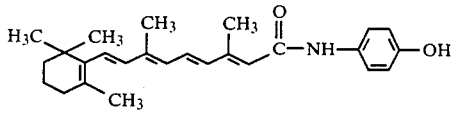

HPR protects against mammary cancer in rats induced with N-nitroso-N-methyl urea, and is less toxic when given orally to rats then retinyl acetate and retinoic acid, see R. C. Moon et al. in Cancer Research, Vol. 39, pages 1339-1346 (1979). When given to rats, one formulation of HPR (5 mg/kg) was incompletely absorbed after oral administration and was eliminated slowly with a half-life of 12 hours, see B. N. Swanson et al. in Drug Metababolism Disposition, Vol. 8 No. 3, pages 168-172 (1980).

In the experimental treatment of cancer described in U.S. Pat. No. 4,323,581, HPR is dissolved in a thioctanoin:ethanol (3:1), Tenox 20 and DL-α-tocopherol solvent system which is then mixed with lab meal. Thus, the HPR is administered by admixture with the diet. HPR is virtually insoluble in water and also quite expensive; administration of tablets or aqueous suspensions of HPR would require ingestion of large quantities of HPR to achieve resonable blood levels of the drug. Efficient administration of pharmaceutically effective levels of HPR to patients is a recognized goal.

The biopharmaceutics of griseofulvin was studied by Philip J. Carrigan in the Journal of Pharmaceutical Sciences, Vol. 62, No. 9, pps. 1476-1479 (1973) wherein an aqueous suspension, a corn oil suspension with polysorbate 60 and a three-phase oil-in-water emulsion containing polysorbate 60, corn oil and water were evaluated. The use of suspensions including vegetable oils and surface active agents for soft gelatin capsules is described at page 371 of "The Theory and Practice of Industrial Pharmacy" Ed. by Leon Lachman, Lea & Febiger, Philadelphia, PA (1970).

SUMMARY OF THE INVENTION

The present invention comprises a novel dosage form of N-(4-hydroxyphenyl)retinamide which provides excellent bioavailability of the active ingredient, in particular oral bioavailability. This would allow administration of significantly smaller amounts of HPR to patients while achieving the desired blood levels of drug as compared to administration of the drug in dry powder, tablet or aqueous suspension forms.

According to the invention, there is provided a composition of HPR, corn oil and a non-ionic surface active agent.

DETAILED DESCRIPTION OF THE INVENTION

The pharmaceutical composition of the invention comprises a suspension of the following components:
(i) N-(4-hydroxyphenyl)retinamide of the following formula:

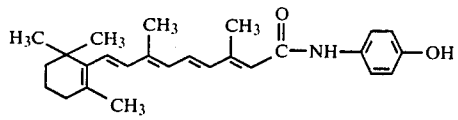

(ii) corn oil; and
(iii) a non-ionic surfactant.

The HPR may be prepared as known in the art, e.g. as described in U.S. Pat. No. 4,323,581.

In addition, it has been found that a small particle size of the HPR tends to aid bioavailability. Thus, mean diameter size of the HPR below about 70 microns is preferred with an optimal range being about 0.5 to 50 microns. The smaller mean diameters of HPR may be achieved through micronization or crystallization. Milling of the HPR to achieve the desired mean particle size may be carried out in a Dynomill Type KD 200c made by Willy A. Bachofen AG of Basel, Switzerland or a Comitrol Model 1500 or 3000 comminuting machine made by Urschel Labs, Inc. of Valparaiso, Ind.

The non-ionic surfactant to be used as the third component of the invention may be any such surfactant suitable for pharmaceutical applications. Examples of these surfactants includes polyethylene sorbitan fatty acid esters, sorbitan fatty acid esters, polyoxyethylene alcohols, polyoxyethylene acids, polyoxyethylene-polyoxypropylene glycols (e.g. the Pluronic surfactants), polyoxyethylated vegetable oils, monoglycerides, diglycerides, polyoxyethylene sorbitol esters, or polysorbates, which are described as fatty acid esters of an anhydrosorbitol which has been etherified with ethylene oxide. Polysorbate 80 is a preferred surfactant and is defined in entry 7455 of the Merck Index, tenth edition, as an oleate ester of sorbitol and its anhydrides copolymerized with about 20 moles of ethylene oxide for each mole of sorbitol and sorbitol anhydrides. Polysorbate surfactants sold under the TWEEN trademark as well as other surface active agents are the subject of the text "Surface Active Agents" by Anthony M. Schwartz et al., Interscience Publishers, Inc., New York (1949), particularly at page 209.

Components (ii) and (iii) are used in the invention particularly in a weight:weight ratio of at least 1:1. Low surfactant amounts are preferred in view of the higher potential for adverse side effects from surfactants compared to the corn oil. Thus, a preferred weight ratio of component (ii):component (iii) is from about 5:1 to 50:1, e.g. about 10:1 to 15:1. The individual doseage of HPR will vary depending on the particular condition being treated and its severity. Normal unit doses are 25, 50, 100 and 175 mg of HPR.

The pharmaceutical composition of the invention is prepared by mixing components (i), (ii) and (iii) in any order although it is preferred to first mix the corn oil and surfactant and then add the desired amount of HPR. The mixing may be carried out in a stainless steel mixing tank. Some mixing also takes place when one decreases the HPR particle size, e.g., in a particle size comminuting device such as the Comitrol made by Urschell Labs, Inc. Alternatively, an in situ mixer-comminuter may be used, e.g., an Arde-Barinco device.

Delivery of the pharmaceutical invention may be by mixing in food, spread on bread or crackers, or by filling the composition in a hard or soft gelatin capsule. A soft gelatin capsule is preferred in view of its ease of storage and availability in a wide variety of shapes an sizes. Rectal or vaginal delivery modes for the suspension in a suppository are also possible. Technology for forming soft gelatin capsules is described in detail in the chapter entitled "Soft Gelatin Capsules" by J. P. Stanley, which is incorporated herein by reference, at pages 359 to 384 of "The Theory and Practice of Industrial Pharmacy", Ed. by Leon Lachman, Lea & Febiger, Philadelphia (1970). The soft gelatin capsules may be formed on a rotary die process machine such as those manufactured by R. P. Scherer of Detroit, Mich. with filling of the capsules as they are formed. Preformed soft gelatin capsules having a small opening may be used by filling the composition through the opening and sealing the hole with a bit of molten soft gelatin. Preferably, the HPR formulation of the invention is given with a meal so as to increase bioavailability. Such a meal may have increased lipid content such as fats, e.g., butterfats, and oils, e.g., animal or vegetable oils. The formulation may be given within 1 hour of such a meal once or twice a day. It has been shown that bioavailability of isotretinoin, e.g., Accutane brand, is affected by food intake, see W. A. Colburn et al. in The Journal of Clinical Pharmacology, Vol. 23, pages 534–539 (1983).

It has been unexpectedly found that administration of HPR in a corn oil/surfactant suspension, compared to other administration modes such as aqueous or neat or even other oil vehicles, provides greatly increased bioavailability of the drug in vivo. This allows the administration of a lower amount of HPR to the patient to achieve the same effect, resulting in lower cost to the patient and lower exposure, at least in the gastric system, to potentially harmful amounts of HPR. Also, part of the present invention is a method for the treatment of breast or bladder cancer, psoriasis or acne, e.g. cystic acne in mammals, e.g. humans, by administration of the pharmaceutical composition of the invention. For an average human of about 70 kg, the daily dose of HPR will be about 100 to 2000 mg per day, e.g. about 300 to 600 mg.

In the following Examples and throughout the specification, the following abbreviations may be used: mg (milligrams); mg/kg (milligrams per kilogram of body weight); g (grams); ng (nanograms); kg (kilograms); ml (milliliters); AUC (area under the plasma concentration versus time curve); ss (steady state); S.E.M. (standard error of the mean); S.D. (standard deviation); v/v (volume to volume ratio); w/w (weight to weight ratio); w/v (weight to volume ratio); hr (hours).

EXAMPLE 1

A. HPR—Aqueous Tragacanth Suspension (Reference)

An aqueous tragacanth suspension of HPR was prepared by suspending HPR in a 0.5% w/v aqueous tragacanth suspension to give a concentration of 80.0 mg/ml of HPR. The required amount of HPR was placed in a mortar and a small amount of 0.5% w/v aqueous tragacanth suspension was added to form a smooth paste on mixing with a pestle. The paste was quantitatively transferred to a precalibrated beaker. Quantitative transfer was affected by multiple rinsings of the mortar with 0.5% w/v aqueous tragacanth suspension. The suspension was made to final volume with 0.5% w/v aqueous tragacanth suspension to give a final concentration of HPR in suspension of 80 mg/ml.

B. HPR—Corn Oil/Tween 80 Suspension (invention)

According to the present invention, an HPR suspension in 11.7:1 (w:w) mixture of corn oil and Tween 80 was prepared by suspending HPR in a mixture of corn oil and Tween 80 11.7:1 (w:w). The required amount of Tween 80 was added to the required amount of corn oil while mixing with an Arde Barinco homogenizer model CJ-4B. The requisite amount of HPR was added to the corn oil-Tween 80 mixture with continued mixing to form a homogeneous suspension which contained a weight ratio of corn oil-Tween 80 mixture to suspended HPR of 7.6:1 (w/w).

Bioavailability Testing (Rats)

HPR suspensions A and B were administered to 48 Crl:COBS. (WI) BR rats comprising 24 male and 24 female rats weighing 150–250 g once daily for 7 days as follows. One group (12 male and 12 female) received Suspension A in the amount of 800 mg of HPR/kg of body weight per day. The other group of rats received Suspension B in the amount of 125 mg of HPR/kg of body weight per day. Administration was by gavage using a curved animal feeding needle such as those supplied by Popper and Sons of New Hyde Park, NY. At 2, 4, and 6 and 24 hours following the seventh dose, six animals (3 male, 3 female) from each group were exsanguinated. Plasma was collected and frozen at −20° C. until assayed. HPR and its N-(4-methoxyphenyl)retinamide metabolite (4-MPR) were separately assayed.

Assay Procedure:

Assay is by high pressure liquid chromatography using a Waters HPLC System consisting of a Model 6000A solvent delivery system with a Model 440 UV absorbance detector (365 nm filter), and either a Model U6K injector (2 ml sample loop) or a Waters Intelligent Sample Processor (WISP TM). Comparable HPLC equipment is acceptable. The column is a 10 cm×4.6 mm (i.d.) Brownlee Labs RP-18 Spheri-5 (5μ) stainless steel column equipped with a 3 cm×4.6 mm (i.d.) Brownlee Labs RP-18 (10μ) stainless steel guard column. The mobile phase is acetonitrile:water:glacial acetic acid (75:23:2, v/v/v) and is prepared in 2 liter quantities. The components of the mobile phase are mixed together, filtered through a 5 μm Millipore ® filter apparatus and degassed under vacuum for one-half hour while stirring. The internal standard for the assay is N-(4-ethoxyphenyl)retinamide (4-EPR). A solution of 4-EPR is prepared by weighing 10.0 mg of 4-EPR into a 100 ml amber tinted volumetric flask and bringing to volume with acetonitrile. A 1/200 dilution of this stock solution is made by transferring 1 ml of the 100 μg/ml 4-EPR solution into a 200 ml volumetric flask and bringing to volume with acetonitrile. The resulting solution contains 500 ng/ml of 4-EPR. This solution is stored in the refrigerator, and has been used for six months without signs of decomposition.

For the assay, a 0.05 ml aliquot of plasma sample is pipetted into a 12×75 mm polypropylene tube (such as the Falcon 2063, Oxnard, CA). Add 1 ml of the internal standard solution and vortex for approximately 30 seconds. After standing for 15 minutes, centrifuge the sample at 600×gravity for 15 minutes at 15° C. A 100 μl aliquot of the supernatant is injected onto the column. The range of retention times which has been observed for each compound, including endogenous retinol, is a follows:

| | |
|---|---|
| HPR: | 3.57–3.85 minutes |
| 4-MPR: | 6.70–7.42 minutes |
| 4-EPR: | 8.29–9.40 minutes |
| Retinol: | 4.79–5.03 minutes |

Reference standard curves (peak height HPR over peak height 4-EPR versus HPR concentration 30–10,000 ng/ml) were prepared daily and the concentration of HPR in samples was determined by mathematical interpolation after weighted (1/variance) linear regression analysis of the standards.

Results:

Results of the assays showed that mean plasma concentrations of HPR and 4-MPR were higher at all time points in animals receiving Suspension B according to the invention, even though Suspension A was given at a far higher dose, see Table I. Mean area under the HPR plasma concentration versus time curve over the dosing interval after the seventh dose was nearly two-fold greater for the oil formulation B compared to the aqueous suspension. This difference was statistically significant (p<0.01).

The ratio of $AUC_{ss}$ (Area under the curve at steady state) to dose was 106.7 for Suspension B versus 8.7 for Suspension A.

TABLE I

| Rat plasma concentrations of HPR (in nanograms/ml) | | | | |
|---|---|---|---|---|
| | Time (hr) After Dosing | | | |
| | 2 | 4 | 6 | 24 |
| Suspension A (800 mg HPR/kg body weight) | | | | |
| Males | 402 | 390 | 281 | 37 |
| | 384 | 533 | 298 | 341 |
| | 615 | 462 | 505 | 272 |
| Females | 283 | 597 | 585 | 77 |
| | 352 | 375 | 237 | 37 |
| | 376 | 210 | 367 | 133 |
| Mean | 402 | 428 | 379 | 150 |
| (S.D.) | (112) | (136) | (138) | (128) |
| $AUC_{ss}$* = 6943 ± 750 (mean ± SEM) | | | | |
| Suspension B (invention) (125 mg HPR/kg body weight) | | | | |
| Males | 986 | 823 | 679 | 186 |
| | 940 | 576 | 813 | 133 |
| | 937 | 1008 | 805 | 63 |
| Females | 1370 | 858 | 987 | 163 |
| | 759 | 1379 | 1048 | 253 |
| | 953 | 641 | 450 | 178 |
| Mean | 991 | 881 | 797 | 163 |
| (S.D.) | (202) | (288) | (216) | (63) |
| $AUC_{ss}$* = 13340 ± 957 (mean ± SEM) | | | | |

*dosing interval = 24 hr; the 24 hr value = 0 hr value

EXAMPLE 2

C. HPR—Dry Powder in Hard Gelatin Capsules 100 mg of HPR was filled by hand into size #1 orange opaque capsules.

D. HPR—Cod Liver Oil/Tween 80 Suspension Soft Gelatin Capsules

The weighed quantities of HPR and Tween 80 were added to cod liver oil in a weight ratio of 25:15:176 while mixing with an overhead mixer. The suspension was mixed until uniform using an Arde Barinco homogenizer. The suspension was then deaerated under vacuum and filled into soft gelatin capsules using a rotary die process machine manufactured by R. P. Scherer of North America. The capsules were dried in shallow trays under controlled temperature and humidity conditions. Each capsule contained 25 mg HPR, 15 mg Tween 80 and 176 mg of cod liver oil.

E. HPR—Corn Oil/TWEEN 80 Suspension Soft Gelatin Capsules (invention)

The manufacturing process for these capsules was the same as that for the cod liver oil Suspension D capsules except that corn oil was used instead of cod liver oil.

F. HPR—Starch/Lactose Hard Gelatin

Weighed quantities of HPR, lactose (hydrous) starch and pregelatinized, starch as follows:

| | |
|---|---|
| HPR | 10 g |
| lactose (hydrous) | 3.5 g |
| starch | 15 g |
| pregelatinized starch | 2 g | were mixed in a mortar and pestle. A 2% solution of sodium lauryl sulfate in purified water (15 ml) was added to the above mixture with trituration. Additional water was added to obtain a suitable granulation. The granules were dried on a paper lined tray in an oven at 48° C. for 6 hours. The granules were reduced in size in a mortar and pestle, weighed and the quantities lost during formulation were calculated. Thus only 2.34 g of modified starch and 0.278 g magnesium stearate were mixed with 25.2 g of granulation. The mixture was filled by hand into size #1 hard gelatin capsules to obtain capsules each containing 100 mg of HPR, 35 mg hydrous lactose, 150 mg starch, 20 mg of pregelatinized starch, 3 mg of sodium lauryl sulfate, 28.6 mg of modified starch and 3.4 mg of magnesium stearate.

Bioavailability Testing (Dogs)

A single oral dose bioavailability study was conducted for HPR in four dogs using the above formulations C, D, E and F. The study was open and 5-way sequential crossover in design with the fifth formulation being a 200 mg HPR formula in an oil other than corn or cod liver which produced plasma concentration lower than either.

A two-week wash-out period was provided between each HPR treatment. Food and water were available ad lib throughout the study. Seven ml blood samples were collected using heparinized Vacutainers ® from each dog at the following times: 0 (predose), 0.5, 1, 2, 3, 4, 6, 8, 10, 12, 24, 48 and 72 hours after dosing with each treatment. Blood samples were collected from the jugular vein by separate venipuncture at each time point. The blood samples were centrifuged in a table top centrifuge and the plasma harvested and kept frozen at −20° C. until analyzed.

Assay Procedure:

The procedure of Example 1 is followed using a 4-EPR internal standard containing 100 μg/ml which is prepared by weighing 10.0 mg of 4-EPR into a 100 ml volumetric flask and bringing to volume with methanol. A 1/2000 dilution of this stock solution is made by transferring 0.1 ml of 100 μg/ml 4-EPR solution into a 200 ml volumetric flask and bringing to volume with methanol. The resulting solution contains 50 ng/ml of 4-EPR. This solution is stored in the refrigerator, and has been used for six months without signs of decomposition. For the assay, a 1.0 ml aliquot of plasma is transferred to a 15 ml screw-cap conical bottomed glass centrifuge tube. Add 1 ml of the internal standard solution and vortex for approximately 15 seconds. Add 4 ml of the extracting solution (3:1 ether:chloroform) and vortex for an additional 15 seconds. Place on a horizontal shaker and mix for 15 minutes. Centrifuge the sample at 600×gravity for 15 minutes at 15° C. Use of a refrigerated centrifuge is recommended to avoid increases in sample temperature during centrifugation that may lead to decomposition of the retinoids. Transfer 3.5 ml of the top 3:1 ether-chloroform layer into another 15 ml screw-cap conical bottomed glass centrifuge tube. Evaporate to dryness under nitrogen. Add 200 μl of 3:1 ethanol:water and vortex for 30 seconds. A 150 μl aliquot of the reconstituted sample is injected onto the column.

Chromatography and quantitation of HPR were performed as described in Example 1.

Treatments C, D, E and F with the respective formulations are summarized as follows:

C: 400 mg of HPR as four hard gelatin capsules each containing 100 mg of HPR as dry powder.

D: 200 mg of HPR as eight soft gelatin capsules each containing 25 mg of HPR, 15 mg of TWEEN 80 and 176 mg of cod liver oil.

E: 200 mg of HPR as eight soft gelatin capsules each containing 25 mg of HPR, 15 mg of TWEEN 80 and 176 mg of corn oil.

F: 200 mg of HPR as two hard gelatin capsules each containing 100 mg of HPR, 35 mg of hydrous lactose, 150 mg of starch, 20 mg of Pregel, 3 mg of sodium lauryl sulfate, 28.6 mg of modified starch and 3.4 mg of magnesium stearate per capsule.

Blood samples were taken at ½, 1, 2, 3, 4, 6, 8, 10, 12, 24, 48 and 72 hours after administration.

Results:

In the following Table II, Peak Plasma Concentrations of HPR are given in nanograms per ml and as a % of Reference Treatment C. Treatment C data are normalized to a 200 mg dose. Also shown is the Area Under the Curve of data for the 72 hour period following administration.

TABLE II

| | Treatment | | | |
|---|---|---|---|---|
| | C | D | E (invention) | F |
| Peak Plasma Concentration (ng/ml) | 431 | 1513 | 1718 | 576 |
| Mean as % of Reference | Ref | 351% | 399% | 134% |
| AUC (0–72 hr) (ng hr/ml) | 7861 | 16481 | 22054 | 8586 |
| Mean as % of Reference | Ref | 210% | 281% | 109% |

EXAMPLE 3

Bioavailability of HPR was compared when administered as a dry powder at 800 and 1600 mg/kg of body weight per day and in a corn oil/surfactant suspension at 125 mg/kg per day. The 800 mg and 1600 mg doses (per kg per day), formulations G and H, respectively, were prepared as in Example 2, formulation C. The 125 mg/kg corn oil suspension, according to the invention, formulation I, was prepared as in formulation B in Example 1 as was the assay procedure. The HPR was administered to four beagle dogs (2M, 2F) daily for 21 days. During the first week, HPR dry powder was administered in hard gelatin capsules at a dose of 800 mg/kg. Plasma samples were collected prior to and 24 hours after the seventh dose. On day 8 the dose of HPR dry powder was increased to 1600 mg/kg. Sampling of plasma was the same as before except that, in addition, plasma was collected prior to the fifth day of this dose. This sampling protocol was also employed during the third week of study when a corn oil/Tween 80 (11.7:1) (w:w) suspension of HPR in hard gelatin capsules was given. All plasma samples were immediately frozen after collection and stored −20° C. until assay.

Results:

Concentrations of HPR are recorded in Table III-A below. Mean peak plasma concentrations of both compounds were in the order: 125 mg/kg/day corn oil/Tween 80 formulation >1600 mg/kg/day dry powder >800 mg/kg/day dry powder. A comparison of the $AUC_{ss}$ derived from the two HPR dry powder doses (Table III-B) revealed a 36% increase in relative exposure (area under the plasma concentration versus time curve at steady-state, $AUC_{ss}$) and a 21% increase in trough plasma HPR concentration for a 2-fold increase in dose. The oil formulation produced a 2.5-fold increase in $AUC_{ss}$ versus the reference (800 mg/kg powder) at one-sixth the dose of HPR. The ratio of $AUC_{ss}$ to dose under these conditions was at least 15-fold greater with the oil formulation than the dry powder formulations.

TABLE III-A

| | Mean for 4 Dogs (ng/ml of plasma) | Standard Deviation |
|---|---|---|
| Formulation G: 800 mg/kg/day - Dry Powder | | |
| Pre-dose #6 | 1276 | 585 |
| Pre-dose #7 | 1370 | 495 |
| 4 hours (h) | 2484 | 855 |
| 6 h | 2532 | 912 |
| 8 h | 2172 | 1030 |
| 24 h | 1032 | 629 |
| $AUC_{ss}$ (ng.h/ml) | 43061 | 18291 |
| Formulation H: 1600 mg/kg/day - Dry Powder | | |
| Pre-dose #5 | 1804 | 521 |
| Pre-dose #6 | 1320 | 500 |
| Pre-dose #7 | 1419 | 566 |
| 4 h | 2434 | 745 |
| 6 h | 3391 | 939 |
| 8 h | 3356 | 706 |
| 24 h | 1414 | 434 |
| $AUC_{ss}$ (ng.h/ml) | 58437 | 11494 |
| Formulation I: (invention) 125 mg/kg/day - Corn Oil/Tween 80 | | |
| Pre-dose #5 | 1864 | 78 |
| Pre-dose #6 | 2164 | 230 |
| Pre-dose #7 | 2217 | 578 |
| 4 h | 7150 | 2298 |
| 6 h | 7265 | 2353 |
| 8 h | 5603 | 1784 |
| 24 h | 1862 | 261 |
| $AUC_{ss}$ (ng.h/ml) | 105727 | 27626 |

TABLE III-B

| | Formulation G 800 mg/kg (powder) | Formulation H 1600 mg/kg (powder) | Formulation I (invention) 125 mg/kg (corn oil/ Tween 80) |
|---|---|---|---|
| $AUC_{ss}$ (ng.h/ml) | 43061 ± 18291 | 58437 ± 11494 | 105727 ± 27626 |
| % Reference | 100 | 136 | 246 |
| $AUC_{ss}$/Dose | 53.8 | 36.5 | 845.8 |
| Peak Concentration (ng/ml) | 2716 ± 1026 | 3607 ± 838 | 7882 ± 2734 |

TABLE III-B-continued

|  | Formulation G 800 mg/kg (powder) | Formulation H 1600 mg/kg (powder) | Formulation I (invention) 125 mg/kg (corn oil/ Tween 80) |
|---|---|---|---|
| Peak Time (h) | 5.5 ± 1.9 | 7.0 ± 1.2 | 5.0 ± 1.2 |
| Trough Concentration (ng/ml) | 1226 ± 561 | 1489 ± 480 | 2027 ± 167 |
| % Reference | 100 | 121 | 165 |

EXAMPLES 4-7

Suspensions of HPR in corn oil and polysorbate 80 may be prepared according to Formulation B as follows:

EXAMPLE 4

A #16 oblong "A" soft gelatin capsule containing

| | |
|---|---|
| 60 mg | Tween 80 |
| 100 mg | HPR |
| 704 mg | corn oil to fil |

EXAMPLE 5

A #16 oblong "A" soft gelatin capsule containing

| | |
|---|---|
| 49 mg | Tween 80 |
| 175 mg | HPR |
| 651 mg | corn oil |

EXAMPLE 6

A #4 oval B soft gelatin capsule containing

| | |
|---|---|
| 15 mg | Tween 80 |
| 25 mg | HPR |
| 176 mg | corn oil |

EXAMPLE 7

A #9½ oblong soft gelatin capsule containing

| | |
|---|---|
| 28 mg | Tween 80 |
| 100 mg | HPR |
| 372 mg | corn oil |

What is claimed is:

1. A pharmaceutical dosage form which comprises a soft gelatin capsule for oral administration containing in the hollow interior thereof, a pharmaceutical composition which comprises a suspension of the following components:

(i) a pharmaceutically effective amount for the treatment of breast cancer, bladder cancer, acne or psoriasis of N-(4-hydroxyphenyl)retinamide of the following formula:

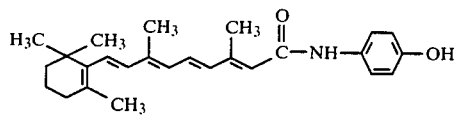

(ii) corn oil; and
    (iii) a non-ionic surfactant, wherein the weight ratio of component (ii):component (iii) is about 5:1 to 50:1.

2. The pharmaceutical dosage form of claim 1, wherein the weight ratio of component (ii):component (iii) is about 10:1 to 15:1.

3. The pharmaceutical dosage form of claim 1, wherein the mean size of the particles of component (i) is below about 70 microns.

4. The pharmaceutical dosage form of claim 3, wherein the mean size of the particles of component (i) is from about 0.5 to 50 microns.

5. The pharmaceutical dosage form of claim 1, wherein said component (iii) is a member of one of the groups consisting of polyethylene sorbitan fatty acid esters, sorbitan fatty acid esters, polyoxyethylene alcohols, polyoxyethylene acids, polyoxyethylene-polyoxypropylene glycols, polyoxyethylated vegetable oils, monoglycerides, diglycerides, polyoxyethylene sorbitol esters, and the polysorbates.

6. The pharmaceutical dosage form of claim 5, wherein said component (iii) is a polysorbate.

7. The pharmaceutical dosage form of claim 6, wherein said component (iii) is polysorbate 80.

8. A method for the treatment of breast cancer, bladder cancer, psoriasis or acne which comprises administering to a mammal in need of such treatment, a pharmaceutically effective amount of the pharmaceutical dosage form of claim 1.

9. The method of claim 8, wherein said method is for the treatment of breast cancer or bladder cancer.

10. The method of claim 9, wherein said cancer is bladder cancer.

11. The method of claim 8, wherein said mammal is a human.

12. The method of claim 8, wherein said administration is with a meal.

13. The method of claim 12, wherein said meal is high in lipids.

* * * * *